United States Patent [19]

Wardlaw

[11] 4,259,012

[45] Mar. 31, 1981

[54] BLOOD COUNT READER

[76] Inventor: Stephen C. Wardlaw, 128 Sunset Hill Dr., Branford, Conn. 06405

[21] Appl. No.: 95,159

[22] Filed: Nov. 19, 1979

[51] Int. Cl.³ .................. G01N 33/48; G01D 9/00; B43L 13/12
[52] U.S. Cl. .................. 356/39; 33/25 B; 33/125 R; 33/143 B; 346/33 ME
[58] Field of Search .......... 356/39, 243; 73/312, 73/149; 33/25 B, 125 R, 125 A, 143 B, 430; 346/33 A, 33 ME

[56] References Cited

U.S. PATENT DOCUMENTS

| | | | |
|---|---|---|---|
| 2,104,525 | 1/1938 | Proskouriakoff | 346/33 ME |
| 2,831,252 | 4/1958 | Weichselbaum | 33/143 B |
| 2,906,025 | 9/1959 | Drummond et al. | 33/125 R |
| 4,027,660 | 6/1977 | Wardlaw et al. | 73/149 |

Primary Examiner—Wm. H. Punter
Attorney, Agent, or Firm—William W. Jones

[57] ABSTRACT

An apparatus for determining hematocrit, white cell and differential white cell and platelet counts in a centrifuged sample of blood contained in a transparent tube, preferably of capillary size. The apparatus is manually operated and utilizes a card which is appropriately calibrated on which the various blood cell counts are recorded.

5 Claims, 3 Drawing Figures

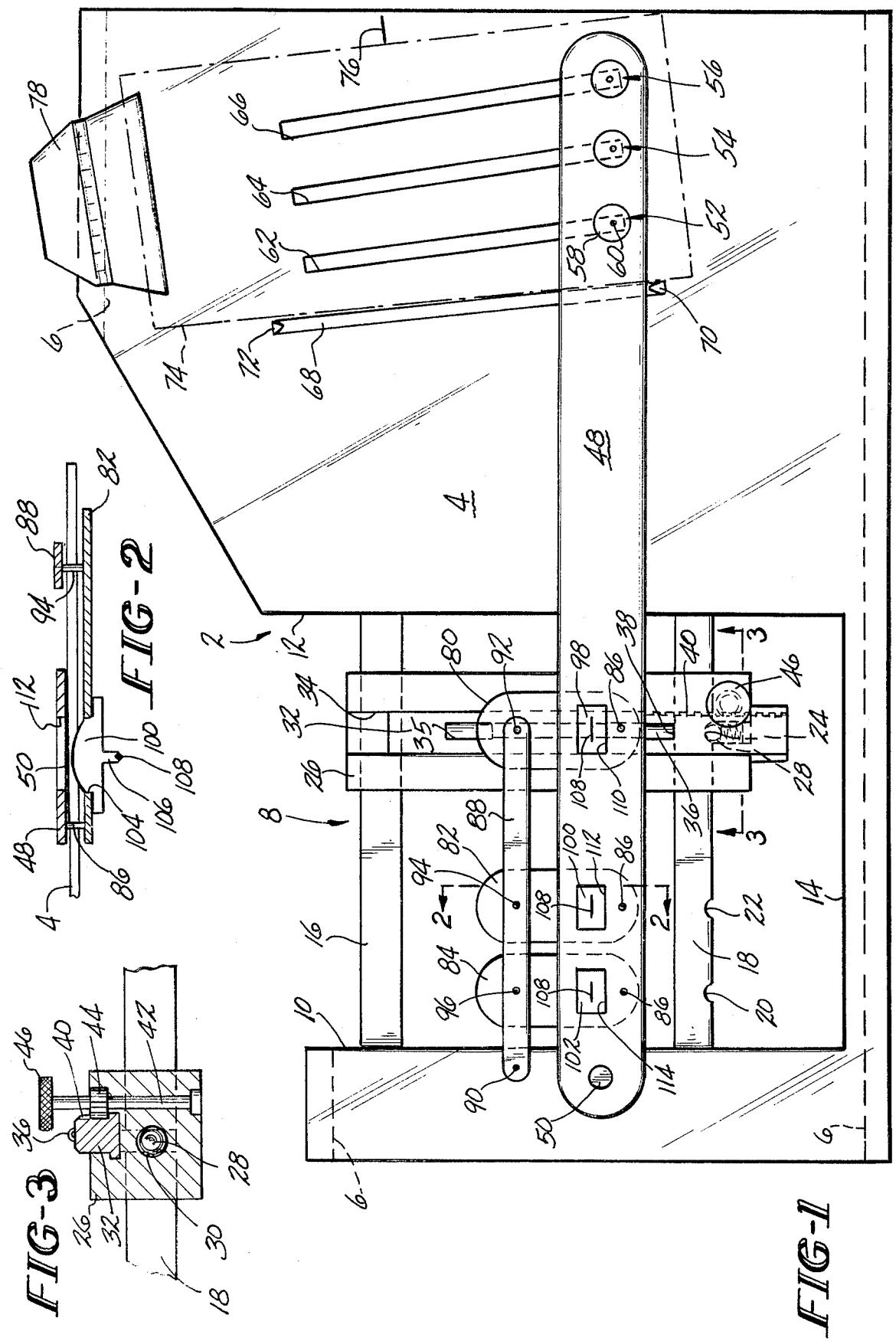

BLOOD COUNT READER

This invention relates to an apparatus for manually reading various blood cell counts from a centrifuged sample of blood contained in a transparent tube. The tube assembly used in conjunction with the apparatus of this invention is described in U.S. Pat. No. 4,027,660, issued June 7, 1977. The apparatus of this invention is used in conjunction with a data card, which card is calibrated and utilized for recording the blood cell counts. The card is disclosed in my co-pending application, Ser. No. 120,558, filed Feb. 11, 1980.

A technique has been developed for measuring blood cell counts using a centrifuged sample of blood contained in a transparent tube, which tube also contains a volume-occupying float which floats on the red cell layer of the centrifuged sample and extends through the white cell layer. This technique is disclosed in U.S. Pat. No. 4,027,660, referred to above.

An electronic instrument has also been developed for use in conjunction with the above-referred to tube-float assembly for reading the various cell counts in the centrifuged sample. The instrument is disclosed in U.S. Pat. No. 4,156,570, issued May 29, 1979.

This invention relates to a manually operable reader instrument which can be used to determine blood cell counts in conjunction with the tube-float assembly referred to above. The instrument of this invention does not require expensive and sophisticated electronics components and is, therefore, less expensive to manufacture. This instrument uses a precalibrated data card upon which is marked the blood cell counts being measured. Details of the card are more fully disclosed in co-pending application, Ser. No. 120,558, as noted above.

It is, therefore, an object of this invention to provide a reader instrument for determining and recording blood cell counts from a centrifuged blood sample.

It is a further object of this invention to provide an instrument of the character described which is manually operable and does not include highly sophisticated electronics components.

It is an additional object of this invention to provide an instrument of the character described which is portable and of durable, yet relatively inexpensive construction.

These and other objects and advantages of this invention will become more readily apparent from the following detailed description of a preferred embodiment of an instrument formed in accordance with this invention, taken in conjunction with the accompanying drawings, in which:

FIG. 1 is a plan view of a preferred embodiment of a reader instrument formed in accordance with this invention;

FIG. 2 is a fragmented sectional view of one of the lens holder parts of the instrument, taken along line 2—2 of FIG. 1; and FIG. 3 is a fragmented sectional view of the stage-operating portion of the instrument, taken along line 3—3 of FIG. 1.

Referring now to the drawings, there is shown in FIG. 1 a preferred embodiment of a manually operated reader instrument formed in accordance with this invention, the instrument being denoted generally by the numeral 2. The instrument 2 includes a generally planar base 4 having downwardly turned side flanges 6 which serve as feet for positioning the base 4 on a flat supporting surface, such as a table or laboratory bench. The base 4 has a generally rectangular cut out portion 8 providing spaced sides 10 and 12 and a bridging side 14. A pair of parallel rails 16 and 18 extend across the cut-out portion 8 between the sides 10 and 12, with opposite ends of the rails 16 and 18 being secured to the base 4. One side of the rail 18 is provided with detent notches 20, 22 and 24. A carrier 26 is slidably mounted on the rails 16 and 18, extend-laterally therebetween, the carrier 26 being reciprocally slidable in the direction of elongation of the rails 16 and 18. A spring loaded ball detent 28 is positioned in a bore 30 (see FIG. 3) in the carrier 26, the detent 28 being engageable with the notches 20, 22 and 24, selectively, to properly position the carrier 26 on the rails 16 and 18. A stage 32 is slidably mounted in a slot 34 in the carrier 26, the stage 32 being reciprocally movable in the direction of elongation of the carrier 26. In the top of the stage 32, there is a slot 35 in which the tube-float assembly 36 is positioned. One end wall 38 of the slot 35 acts as a positioning stop for the end of the tube-float assembly 36 in which the red cells are packed. The carrier 26 and stage 32 can be made from transparent or translucent plastic to allow for rear lighting of the blood sample during the reading procedure, or appropriate slots can be formed in the carrier 26 and stage 32 for transmission of light to the blood sample. An electrical light source (not shown) can be mounted on the bottom of the carrier 26 in an appropriate manner and can be illuminated either by a battery pack or with house current.

Reciprocal movement of the stage 32 with respect to the carrier 26 can be accomplished with a rack and pinion drive. One side surface 40 of the stage 32 can be formed with teeth to provide the rack. A pin 42 is rotatably journaled in the carrier 26 and carries a pinion gear 44 which engages the rack 40. A knob 46 is mounted on the top of the pin 42 for facilitating rotational manipulation of the pin 42 and pinion gear 44. It will be appreciated that clockwise or counterclockwise rotation of the pinion gear 44 will cause reciprocal sliding movement of the stage 32 to occur over the carrier 26. In this manner, alignment movement of the tube-float assembly 36 is achieved. Details of the above-described arrangement are shown in FIG. 3.

An axially elongated arm 48 is mounted on the base 4 for pivotal movement with respect to the base 4, such pivotal movement occurring about a pin 50 which mounts the arm 48 on the base 4. Mounted on the end of the arm 48 opposite the pin 50 are three manually actuable marking devices 52, 54 and 56. The marking devices each comprise an enlarged head 58 having a needle 60 mounted on the underside thereof, which needle 60 can project through an aligned opening in the arm 48. The needles 60 and heads 58 are normally biased upwardly by a spring so that the needles 60 do not project substantially below the arm 48. Manually, the head 58 can be pressed against the force of the spring to cause the needle 60 to project past the arm 48. There are three elongated slots 62, 64 and 66 opening through the base 4, one of each of the slots being aligned with a respective one of the marking devices. Thus, when one of the buttons is pressed, the respective needle will project past the arm 48 and into the respective slot aligned with the pressed needle. When the button is released, the needle will move back to its retracted position by reason of the spring associated therewith.

A raised rib or flange 68 extends upwardly from the top surface of the base 4 and supports the underneath side of the arm 48 so that the arm 48 slides over the rib 68 as the arm 48 is pivoted about the pin 50. A pair of motion limiting stops 70 and 72 project upwardly from the top surface of the rib 68 and act to limit the extent to which the arm 48 can be pivoted about the pin 50. The rib 68 also serves as a locator for a data card 74 (shown in phantom) which is placed on the top surface of the base 4, beneath the arm 48. An index mark 76 is disposed on the top surface of the base 4 for alignment with a matching index mark on the card 74. Once properly aligned, the data card 74 is temporarily secured to the base 4 by means of a manually operable clip 78. It will be noted that the card 74, when in position, overlies the slots 62, 64 and 66. Thus, when the needles 60 are pressed, they will punch holes in the card 68 on parts of the card overlying the slots 62, 64 and 66.

Three lens supports 80, 82 and 84 are provided on the instrument 2. Each lens support has one of its ends pivotally connected to the arm 48 by means of a pin 86, the supports 80, 82 and 84 being disposed beneath the arm 48. Adjacent to the arm 48, an elongated link 88 is pivotally connected to the base 4 by means of a pin 90. The opposite end of the link 88 is pivotally connected to the lens support 80 by means of a pin 92. Additional pivotal connections are provided between the lens supports 82 and 84 and the link 88 by means of pins 94 and 96, respectively. The pivotal connections between the arm 48, the lens supports 80, 82 and 84, and the link 88 are such that the link 88 and the arm 48 are maintained in parallel alignment during pivoting of the arm 48 about the pin 50. Mounted in each lens holder 80, 82 and 84, there are optically magnifying lenses 98, 100, and 102, respectively. As noted in FIG. 2, the lenses, as 100, may be cemented to the underside of the lens supports, as 82, and the convex upper surface of the lens 100 projects through an opening 104 in the lens support 82. Each lens 98, 100, and 102 preferably includes a downwardly extending flange or rib 106 on the lower surface of which there is disposed an opaque reference line 108 which is visible through the lens. Disposed above each lens 98, 100 and 102, there is a window 110, 112 and 114, respectively, cut through the arm 48 so that one may view the optically magnified images through the arm 48.

The instrument 4 operates as follows. The marking device 52 and the lens 98 are used conjointly to measure the relative red cell volume (hematocrit); the marking device 54 and the lens 100 are used conjointly to measure the granulocyte cell count; the marking device 54 and the lens 102 are used conjointly to measure the white blood cell count; and the marking device 56 and the lens 102 are used conjointly to measure the platelet count.

Details of the card 74, as noted previously, are set forth in co-pending application, Ser. No. 120,558, suffice to say, however, that the card 74 has printed on it three adjacent scales which, when the card is in place on the instrument, overlie the slots 62, 64 and 66. The scale overlying the slot 62 is used to measure the relative red blood cell volume (hematocrit), the scale overlying the slot 64 is used to measure the granulocyte and white blood cell counts, and the scale which overlies the slot 66 is used to measure the platelet count. Thus, the marker 52 will be termed the RBC marker, the marker 54 will be termed the GRAN/WBC marker, and the marker 56 will be termed the PLT marker. The lens 98 is the red blood cell viewing lens, the lens 100 is the granulocyte cell viewing lens, and the lens 102 is the white blood cell and platelet viewing lens.

The card 74 is properly aligned on the instrument 2 and held in place with the clip 78. A centrifuged blood sample-containing tube 36 is placed in the stage slot 35, with the red blood cell containing end of the tube being abutted against the end wall 38 of the slot 35. The arm 48 is pivoted about the pin 50 so as to abut the stop 70. The stage 32 is then moved by manipulating the knob 46 until the lower end of the red blood cell layer is aligned with the reference line 108 on the lens 98. The arm 48 is then pivoted in a counter-clockwise direction about the pin 50 and slid over the rib 68 until the reference line 108 on the lens 98 is aligned with the bottom surface of the float member which is in the tube. While so aligned, the RBC marker 52 is depressed so as to punch a hole in the card 74 at the appropriate location on the RBC scale on the card. After releasing the RBC marker 52, the arm 48 is pivoted back about the pin 50 until the arm 48 again abuts the stop 70. The carrier 26 is then moved to the left as viewed in FIG. 1 until the detent notch 22 is engaged. The tube 36 is then disposed beneath the lens 100. The stage 32 is then moved by manipulating the knob 46 until the red blood cell-granulocyte cell interface is aligned with the reference line 108 on the lens 100. The arm 48 is then pivoted in a counter-clockwise direction about the pin 50 until the reference line 108 on the lens 100 is aligned with the granulocyte-mononuclear cell interface at which time the GRAN/WBC marker 54 is depressed to punch a hole in the card 74 at an appropriate place in the GRAN/WBC scale on the card 74. Thus, the granulocyte cell count is made. While keeping the GRAN/WBC marker 54 depressed to hold the arm 48 in position, the carrier 26 is again moved to the left until the detent notch 20 is engaged, whereby the tube 36 is disposed beneath the lens 102. A bayonet slot-lug arrangement may be provided on the GRAN/WBC marker 54 so that twisting the same can lock the marker 54 in its depressed state. Once the tube 36 is disposed beneath the lens 102, the stage 32 is moved by manipulating the knob 46 until the granulocyte-mononuclear cell interface is aligned with the reference line 108 on the lens 102. The GRAN/WBC marker 54 is then released and the arm 48 is pivoted about the pin 50 until the reference line 108 on the lens 102 is aligned with the mononuclear cell-platelet interface whereupon the GRAN/WBC marker 54 is again depressed punching a second hole in the GRAN/WBC scale on the card 74. Thus, the total white blood cell count is registered on the card 74. The arm 48 is then pivoted clockwise about the pin 50 to return the arm 48 into abutment with the stop 70. The stage 32 is then moved by manipulating the knob 46 to align the mononuclear cell-platelet interface with the reference line 108 on the lens 102. The arm 48 is then pivoted in a counter-clockwise direction about the pin 50 until the reference line 108 on the lens 102 is aligned with the platelet-plasma interface at which time the PLT marker 56 is depressed punching a hole in the card 74 at the appropriate place in the PLT scale on the card 74, whereby the platelet count is registered on the card 74.

It should be noted that, while needle-type markers are preferred for use with the instrument, alternative markers which use a marking fluid or the like can be used without departing from the inventive concept. The viewing lenses can be made from clear plastic, glass, or the like, or can be made from tinted or specially coated materials which will enhance the appearance of the color differentiation present in the cells being measured. It will also be noted that the pivotal mounting arrangement for the lenses keeps the reference lines relatively perpendicular to the axis of the specimen tube as the reader arm is pivoted during the readings.

It will be readily appreciated that the instrument of this invention can be relatively inexpensively manufactured and operates without the need of sophisticated electronics components. It can be made relatively portable and lightweight and is relatively durable. The accuracy of readings obtained is controlled by the reading radii of the reading arm, proper control of these radii enabling one to use scales on the printed card of appropriate lengths so as to ensure accuracy. The reason that the granulocyte cell band is measured with a different lens than the mononuclear cell band is because of the different cell sizes and packing characteristics between the two different cell types. Thus, the instrument automatically corrects for the different cell sizes found in whole blood samples.

It is to be understood that the above constitutes a description of a preferred embodiment of the invention and that the scope of the invention is not to be limited otherwise than as required by the appended claims.

What is claimed is:

1. An improved instrument for use in measuring blood cell counts in a centrifuged blood sample, said instrument comprising:
    (a) a stage for supporting a tube containing a centrifuged sample of whole blood, the cell counts of which are to be measured, said stage being movable in the direction of elongation of the blood-containing tube when the latter is disposed on the stage;
    (b) at least two optically magnifying lenses for viewing the tube when the latter is disposed on the stage, each lens having associated therewith a reference line for alignment with cell type interfaces in the centrifuged blood sample;
    (c) means for moving said stage between at least two positions, each of which positions enables the tube, when disposed on the stage, to be viewed by a different one of said lenses;
    (d) a movable member operably connected to each of said lenses for moving said lenses in the direction of elongation of the tube when the tube is disposed on the stage;
    (e) at least two marking means operably connected to said movable member for movement therewith, each of said marking means being associated with a respective lens and reference line;
    (f) mounting means for temporarily holding a data card adjacent to said marking means whereby the card can be marked by said marking means when an associated reference line is aligned with a particular cell interface in the centrifuged blood sample; and
    (g) means for controlling the extent of movement of each of said marking means so that one of said marking means will move a greater distance than the other when its associated reference line is moved the same distance along the tube as the other reference line, whereby compensation is had for different cell sizes and packing characteristics.

2. An improved instrument for use in measuring blood cell counts in a centrifuged blood sample, said instrument comprising:
    (a) a base;
    (b) a stage mounted on said base for bilateral movement with respect to said base, said stage being operable to support a tube containing a centrifuged blood sample, said stage being movable in a first direction coinciding with the direction of elongation of the tube when the latter is disposed on the stage, and in a second direction perpendicular to said first direction;
    (c) at least two optically magnifying lenses for viewing the tube when the latter is disposed on said stage, each lens having associated therewith a reference line for alignment with cell type interfaces in the centrifuged blood sample, said lenses being spaced apart from each other in said second direction;
    (d) a member pivotally mounted to said base;
    (e) means operably interconnecting said member and said lenses to cause said lenses and reference lines to move in said first direction when said member is pivotally moved with respect to said base;
    (f) at least two marking devices operably connected to said member for movement therewith, each of said marking devices being associated with a respective lens and reference line, said marking devices being spaced apart from each other in said second direction; and
    (g) mounting means for temporarily securing a data card to said base adjacent to said marking devices whereby the card can be marked by each of said marking devices when an associated reference line is aligned with a particular cell interface in the centrifuged blood sample.

3. The instrument of claim 2, further comprising means for maintaining said reference lines substantially parallel to said second direction during movement of said lenses and reference lines in said first direction.

4. An improved instrument for use in measuring blood cell counts in a centrifuged blood sample, said instrument comprising:
    (a) a base;
    (b) a stage mounted on said base for bilateral movement with respect to said base, said stage being adapted to support a tube containing a centrifuged blood sample, said stage being movable in a first direction coinciding with the direction of elongation of the tube when the latter is disposed on the stage, and in a second direction perpendicular to said first direction;
    (c) a measuring member mounted on said base by means of a pivot whereby said measuring member can be pivotally moved with respect to said base, said pivot being disposed adjacent to one end of said measuring member;
    (d) a plurality of optically magnifying viewing lens assemblies connected to said measuring member for viewing a tube mounted on said stage, each of said lens assemblies being spaced apart a different distance from said pivot than the others of said lens assemblies, each of said lens assemblies being provided with means forming a reference line, and each of said lens assemblies being movable in said first direction when said measuring member is pivoted with respect to said base;
    (e) marking means mounted on said measuring member remote from said pivot; and
    (f) mounting means for temporarily securing a data card to said base adjacent to said marking means whereby said marking means can mark the data card.

5. The instrument of claim 4, further including means for maintaining said reference lines substantially perpendicular to said first direction during pivotal movement of said measuring member.

* * * * *